(12) United States Patent
Mansour (10) Patent No.: US 9,335,455 B2
(45) Date of Patent: *May 10, 2016

(54) EXTENDED TIP LASER AND ILLUMINATION PROBE FOR RETINA SURGERY

(71) Applicant: Cygnus LP, Roswell, GA (US)

(72) Inventor: Fouad Mansour, Sandy Springs, GA (US)

(73) Assignee: Cygnus, LP, Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,693

(22) Filed: May 29, 2013

(65) Prior Publication Data

US 2013/0322108 A1    Dec. 5, 2013

Related U.S. Application Data

(60) Provisional application No. 61/652,992, filed on May 30, 2012.

(51) Int. Cl.
*A61B 18/22* (2006.01)
*F21V 8/00* (2006.01)
*A61F 9/008* (2006.01)

(52) U.S. Cl.
CPC .............. *G02B 6/0005* (2013.01); *A61B 18/22* (2013.01); *A61F 9/00821* (2013.01); *A61B 2018/2222* (2013.01); *A61F 2009/00863* (2013.01)

(58) Field of Classification Search
CPC ............ G02B 6/0008; G02B 27/0994; G02B 23/2469; H01S 5/005; H01S 5/02284; A61B 2019/5206; A61B 19/5202; A61B 1/07

USPC .......................... 362/551, 553, 554, 572, 574
See application file for complete search history.

(56) References Cited

U.S. PATENT DOCUMENTS

| 4,029,391 A | 6/1977 | French |
| 5,123,902 A | 6/1992 | Muller et al. |
| 5,147,353 A * | 9/1992 | Everett ............................ 606/15 |

(Continued)

FOREIGN PATENT DOCUMENTS

| EP | 682910 | 11/1995 |
| WO | WO 98/24513 | 6/1998 |
| WO | WO 2009/058498 | 5/2009 |

OTHER PUBLICATIONS

International Patent Application No. PCT/US2012/059446: International Search Report and Written Opinion dated Jan. 2, 2013, 12 pages.

(Continued)

*Primary Examiner* — Julie Bannan
*Assistant Examiner* — Meghan Ulanday
(74) *Attorney, Agent, or Firm* — Kaplan Intellectual Property Law, LLC (57) ABSTRACT

An illumination and laser energy delivery system, including an extended tip laser and illumination probe for retinal surgery, is disclosed that allows efficient delivery of laser and illumination energy to a surgical site through a device that is smaller than the standard 20 gauge probe conventionally used in endo-photocoagulation procedures. Novel constructions, as disclosed, enable the space inside the probe cannula to be used more efficiently than in prior art devices, providing improved performance of the device and system in delivering laser and illumination energy to the surgical site.

23 Claims, 5 Drawing Sheets

(56) References Cited

U.S. PATENT DOCUMENTS

| | | |
|---|---|---|
| 5,156,604 A | 10/1992 | Hessel et al. |
| 5,217,465 A | 6/1993 | Steppe |
| 5,231,989 A | 8/1993 | Middleman et al. |
| 5,275,593 A | 1/1994 | Easley et al. |
| 5,281,214 A | 1/1994 | Wilkins et al. |
| 5,300,061 A | 4/1994 | Easley et al. |
| 5,323,766 A | 6/1994 | Uram et al. |
| 5,372,585 A | 12/1994 | Tiefenbrun et al. |
| 5,409,457 A | 4/1995 | Del Cerro et al. |
| 5,447,512 A | 9/1995 | Wilson et al. |
| 5,512,034 A | 4/1996 | Finn et al. |
| 5,520,222 A | 5/1996 | Chikama |
| 5,603,710 A | 2/1997 | Easley et al. |
| 5,651,783 A | 7/1997 | Reynard |
| 5,656,011 A | 8/1997 | Uihlein et al. |
| 5,722,970 A | 3/1998 | Colvard et al. |
| 5,741,225 A | 4/1998 | Lax et al. |
| 5,891,022 A | 4/1999 | Pologe |
| 6,015,403 A | 1/2000 | Jones |
| 6,110,195 A | 8/2000 | Xie et al. |
| 6,197,003 B1 | 3/2001 | Howard et al. |
| 6,572,608 B1 | 6/2003 | Lee et al. |
| 6,575,989 B1 | 6/2003 | Scheller et al. |
| 6,616,628 B2 | 9/2003 | Hayzelden |
| 6,984,230 B2 | 1/2006 | Scheller et al. |
| 7,141,048 B1 | 11/2006 | Charles |
| 7,189,226 B2 | 3/2007 | Auld et al. |
| 7,267,674 B2 | 9/2007 | Brucker et al. |
| 7,402,158 B2 | 7/2008 | Scheller et al. |
| 7,473,249 B2 | 1/2009 | Scheller et al. |
| 7,766,904 B2 | 8/2010 | McGowan, Sr. et al. |
| 7,909,816 B2 | 3/2011 | Buzawa |
| 7,922,645 B2 | 4/2011 | Kaplan |
| 8,317,778 B2 | 11/2012 | Spaide |
| 2003/0088257 A1 | 5/2003 | Awh et al. |
| 2005/0113814 A1 | 5/2005 | Loeb |
| 2005/0154379 A1 | 7/2005 | McGowan et al. |
| 2005/0288555 A1 | 12/2005 | Binmoeller |
| 2006/0004348 A1 | 1/2006 | Scheller et al. |
| 2006/0173448 A1 | 8/2006 | Scheller et al. |
| 2007/0100401 A1 | 5/2007 | Lin |
| 2007/0265602 A1 | 11/2007 | Mordaunt et al. |
| 2007/0288043 A1 | 12/2007 | Rehnke |
| 2008/0058704 A1 | 3/2008 | Hee et al. |
| 2008/0097415 A1 | 4/2008 | Zimare et al. |
| 2008/0188910 A1 | 8/2008 | Spaide |
| 2008/0195044 A1 | 8/2008 | Nishimura |
| 2008/0262442 A1 | 10/2008 | Carlin et al. |
| 2008/0275435 A1* | 11/2008 | Nadolski ............ 606/15 |
| 2009/0093800 A1 | 4/2009 | Auld et al. |
| 2009/0118715 A1 | 5/2009 | Mansour |
| 2010/0004642 A1 | 1/2010 | Lumpkin |
| 2010/0076503 A1 | 3/2010 | Beyar et al. |
| 2010/0204716 A1 | 8/2010 | Stewart et al. |
| 2011/0125139 A1 | 5/2011 | Auld et al. |
| 2011/0190683 A1 | 8/2011 | Gellman et al. |
| 2013/0090635 A1 | 4/2013 | Mansour |

OTHER PUBLICATIONS

Schena, "Virectomy and the Vanishing Suture", Mar. 2003, Eye Net, American Academy of Ophthalmology, 28-31.

Thierry et al., "Blood Compatibility of Nitinol Compared to Stainless Steel", Proceedings of the International Conference on Shape Memory and Superelastic Technologies, 2000, SMTS-2000, 7 pages.

\* cited by examiner

Figure 2D

EXTENDED TIP LASER AND ILLUMINATION PROBE FOR RETINA SURGERY

CROSS-REFERENCE TO RELATED APPLICATIONS

The present United States non-provisional patent application claims priority to, and full benefit of, U.S. provisional patent application Ser. No. 61/652,992, filed on May 30, 2012, entitled "Extended Tip Laser and Illumination Probe for Retinal Surgery," the disclosure of which is incorporated by reference herein as though set forth in its entirety.

TECHNICAL FIELD

The subject matter of the present invention relates, generally, to probes for endo-photocoagulation laser treatment at the retina during eye surgery; and relates, more particularly, to probes combining more than one function within the same probe for use in association with retinal surgery.

BACKGROUND

In the field of endo-photocoagulation laser treatment at the retina during eye surgery, it is desirable to combine more than one function in the same probe. Different designs have been in use to address this issue.

Most often, means for delivering laser and illumination energy to the treatment site are combined via a single cannula. This arrangement is generally advantageous in order to reduce the trauma to the eye (by having one less entry point), to release the doctor's hand from having to manipulate an extra instrument, and to provide better targeting of the treatment site.

As the industry has moved towards smaller cannulas (typically, 25 gauge and 23 gauge, as opposed to the larger, 20 gauge cannula) that hold fiber optics for both laser and illumination, less space is available to accommodate the fiber optics. Accordingly, in smaller cannulas, the design tendency has been to reduce the diameter of the illumination and/or laser fibers, which disadvantageously results in lower efficiency levels.

As the technology has evolved, however, it was found that extending the laser tip beyond the illumination fiber by about 3 mm offers better results, partly by allowing greater illumination area coverage at the treatment site.

Currently, the larger, 20 gauge size has enough space to accommodate the illumination fiber optic, having its tip flush with the probe cannula and, on the side and contained within the same probe cannula, a laser fiber optic that extends about 3 mm beyond the tip of the illumination fiber optic. As the laser fiber optic would have no protection against breakage inside the eye, a tube holds the laser fiber optic and extends into the probe cannula, running parallel with the illumination fiber optic.

Scaling down such a design from 20 gauge to the smaller sizes described above has an adverse effect on the performance of the device. For example, with smaller probe cannulas, protecting the laser fiber optic with a tube consumes valuable area and forces the designer to reduce the illumination fiber diameter to a level that renders it much less capable of delivering enough light to the surgical site.

On the other hand, having a smaller laser fiber optic helps provide more space for the illumination fiber, but poses a new set of challenges for alignment of the laser source with the smaller fiber optic.

Accordingly, it would be advantageous to provide one or more solutions to the aforedescribed problems. Such a solution would deliver an appropriate amount of both illumination and laser energy to a surgical site, and would allow the fiber optic delivery system for both energy sources to be housed within a single cannula of any of the standard sizes. It is to the provision of such solutions that the present disclosure is directed.

SUMMARY

In recognition of the above-described problems, two solutions are herein proposed. In a first proposed solution, instead of using two fibers side by side, an illumination ring or tube, acting as the illumination fiber optic, surrounds the laser fiber optic that is protected with a tube against breakage. Advantageously, all gaps between the two, separate fiber optics are eliminated and the space is utilized to its full capacity. In a second proposed solution, instead of using a tube to protect the extended laser fiber optic, the end of the probe cannula is cut so as to provide "side protection" for the laser fiber optic, in conjunction with adhesives that adhere the fiber optic to the extended part of the cannula. Alternatively, the same extended portion of the cannula may be folded around the laser fiber optic, providing increased mechanical integrity.

In a first embodiment, a tube that provides high illumination transmission is preferably polished at both ends. A laser fiber optic is inserted into a protective sheath, such as a stainless steel tube. Alternatively, the laser fiber optic can be manufactured with one or more layer of material that acts to strengthen the fiber optic and protect it. An illumination tube or ring surrounds the combined laser fiber optic and protective sheath, allowing approximately 3 mm of the combined laser fiber optic and protective sheath to be extended. The illumination tube or ring, along with the protected laser fiber optic are inserted into the probe cannula, the illumination tube or ring being proximate the tip of the cannula, and preferably not into it, so as not to reduce the illumination. The back of the illumination tube or ring is separated from the laser fiber optic and coupled to one or more fiber optics that provide light to be transmitted to the front of the illumination tube or ring and into the surgical site. The illumination tube or ring can be pre-made or cast where needed. In some embodiments, enhancing the light output can be achieved by coating one or both sides of the illumination tube or ring with materials having different indices of refraction, as is common in the design of fiber optics.

In a second embodiment, lateral cutting of approximately 3 mm is performed at the end of the probe cannula. The depth of the cut may be as much as the mechanical integrity of the remaining extension allows, taking into consideration that an adhesive that bonds the laser fiber optic to the extension may add to the strength and integrity. The depth of the cut contributes to a better spread of the light from the illumination fiber optic and reduces the shadow of the extended tip. In an alternate embodiment, the depth of the cut is calculated so that when folded over the laser fiber optic, most of the laser fiber optic is surrounded with the folded extension. Although a sharp cut at the base of the extension provides a consistent overall diameter of the extension after folding, a rounded cut may, in some embodiments, be preferred. With a rounded cut, the starting point of the cut may start rounded and continues gradually to become a straight cut parallel to the tube length. Such a rounded cut beneficially may provide better strength at the base of the cut and, therefore, increased overall mechanical strength. It is noted that, while such a rounded cut provides increased mechanical integrity, it may reduce the folding length to less than the full length.

These and other features and advantages of the various embodiments of devices and related systems, as set forth within the present disclosure, will become more apparent to those of ordinary skill in the art after reading the following Detailed Description of Illustrative Embodiments and the Claims in light of the accompanying drawing Figures.

BRIEF DESCRIPTION OF THE DRAWINGS

Accordingly, the within disclosure will be best understood through consideration of, and with reference to, the following drawing Figures, viewed in conjunction with the Detailed Description of Illustrative Embodiments referring thereto, in which like reference numbers throughout the various Figures designate like structure, and in which.

It is to be noted that the drawings presented are intended solely for the purpose of illustration and that they are, therefore, neither desired nor intended to limit the invention to any or all of the exact details of construction shown, except insofar as they may be deemed essential to the claimed invention.

DETAILED DESCRIPTION OF ILLUSTRATIVE EMBODIMENTS

In describing the several embodiments illustrated in the Figures, specific terminology is employed for the sake of clarity. The invention, however, is not intended to be limited to the specific terminology so selected, and it is to be understood that each specific element includes all technical equivalents that operate in a similar manner to accomplish a similar purpose. Additionally, in the Figures, like reference numerals shall be used to designate corresponding parts throughout the several Figures.

Figures 1A, 1B:
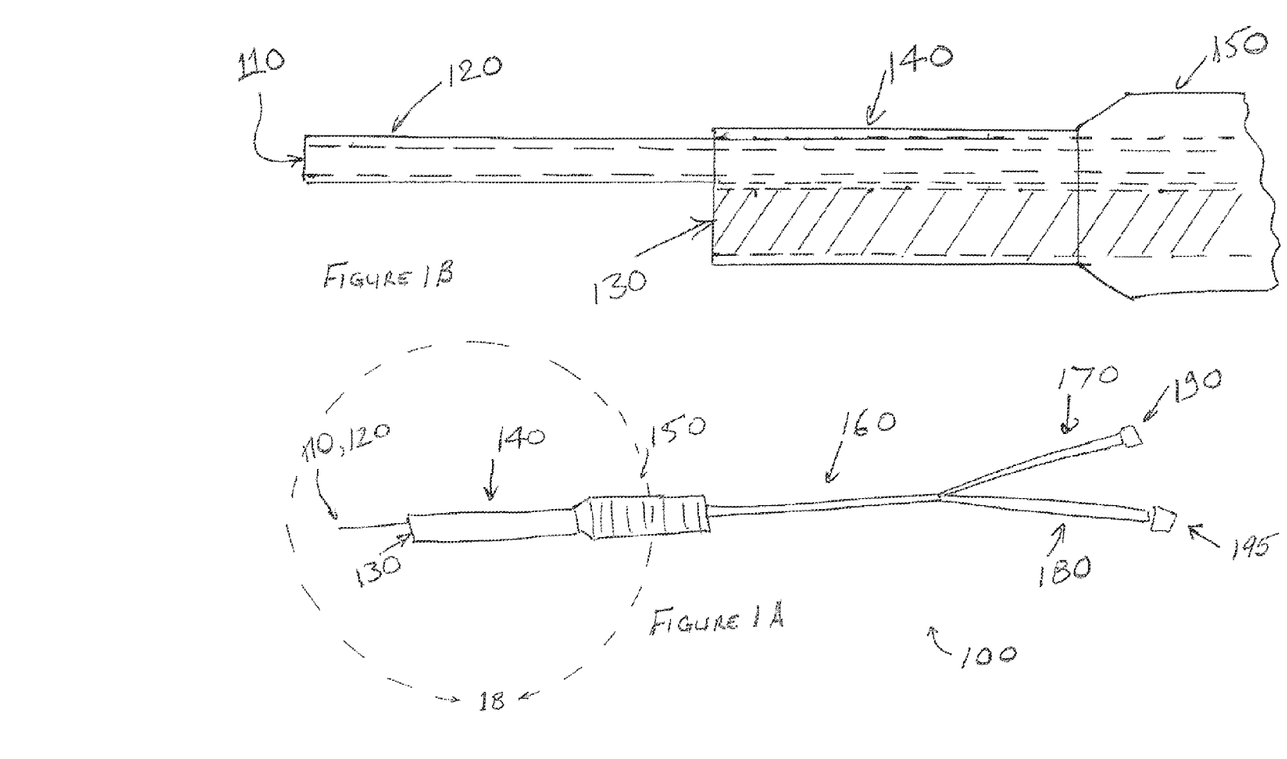
FIG. 1A illustrates a representative, prior art illumination and laser energy delivery system.
FIG. 1B illustrates an enlarged view of a portion of the representative, prior art illumination and laser energy delivery system depicted in FIG. 1A.
Figures 2A, 2B, 2C:
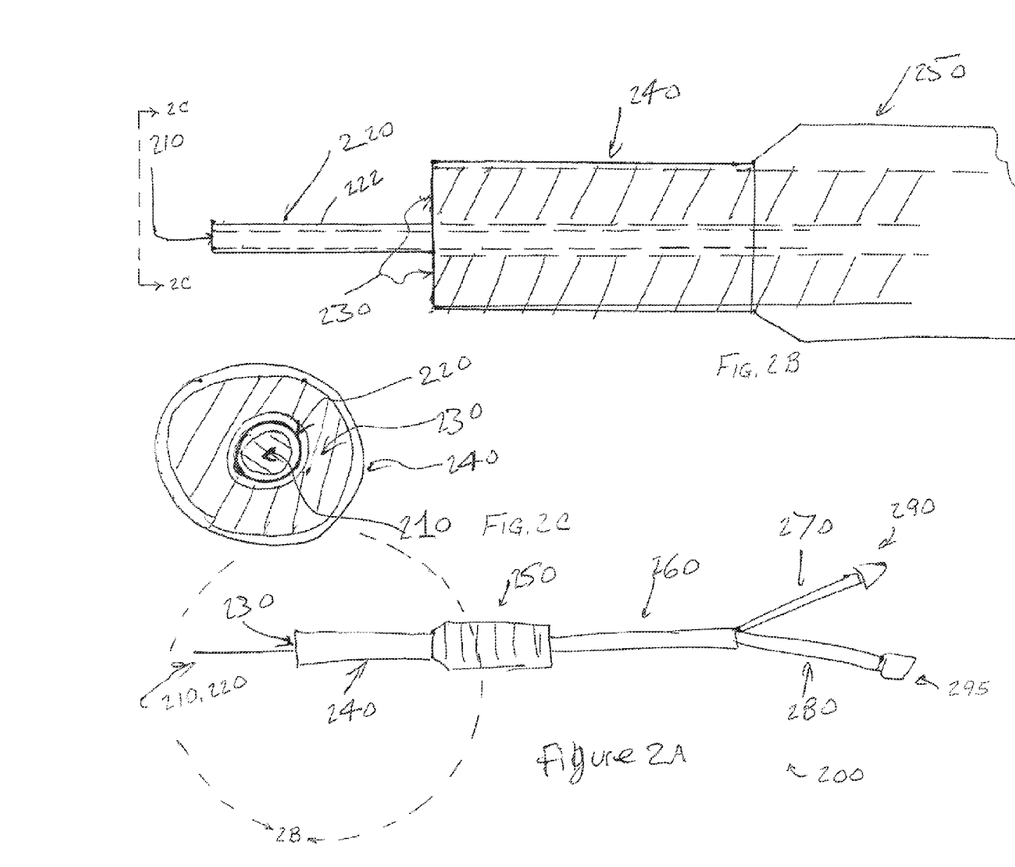
FIG. 2A illustrates a first embodiment of an illumination and laser energy delivery system, including an extended tip laser and illumination probe for retinal surgery, according to the present disclosure.
FIG. 2B illustrates an enlarged view of a portion of the extended tip laser and illumination probe for retinal surgery depicted in FIG. 2A.
FIG. 2C illustrates an enlarged end view of a portion of the extended tip laser and illumination probe for retinal surgery depicted in FIG. 2B.
Figure 2D:
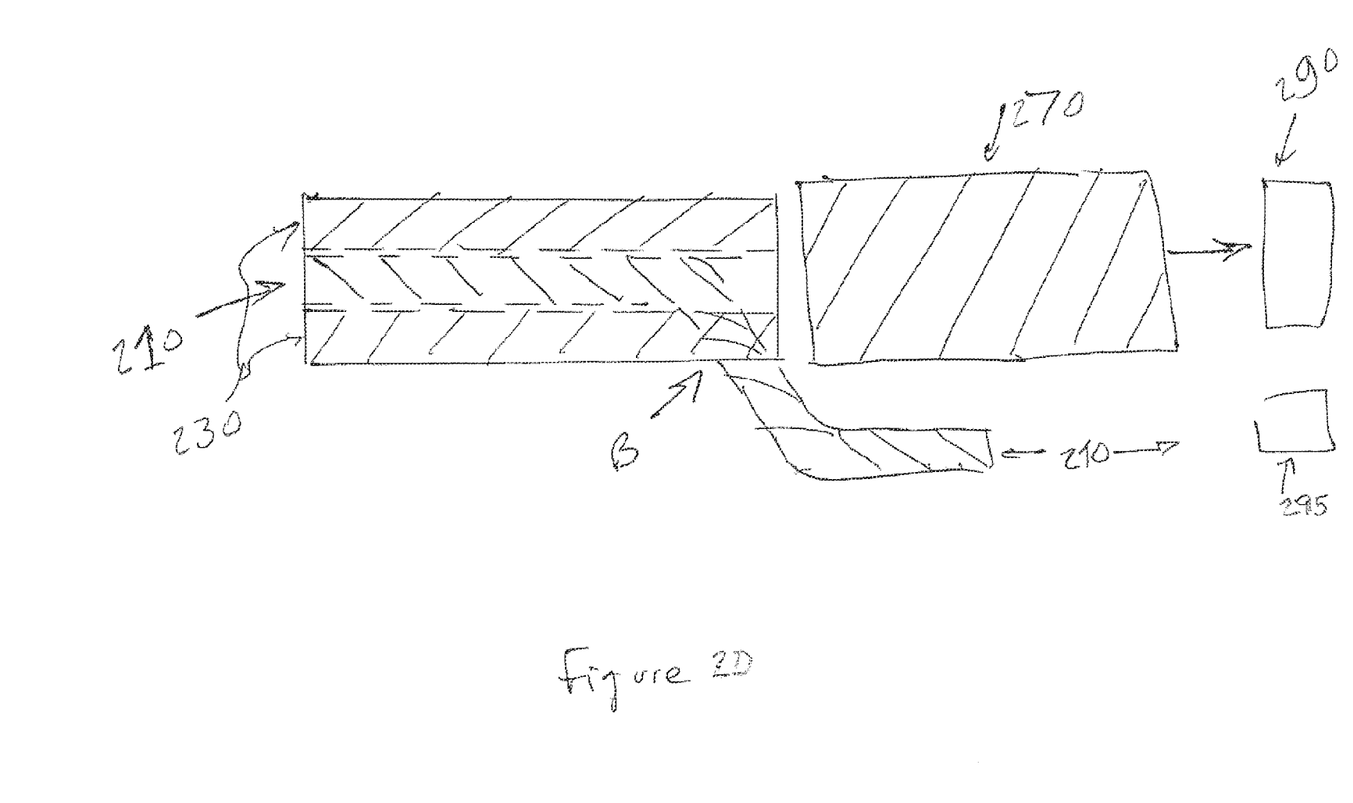
FIG. 2D illustrates certain coupling details attendant the first embodiment of an illumination and laser energy delivery system, including an extended tip laser and illumination probe for retinal surgery, depicted in FIG. 2A.
Figures 3A, 3B, 3C, 3D:
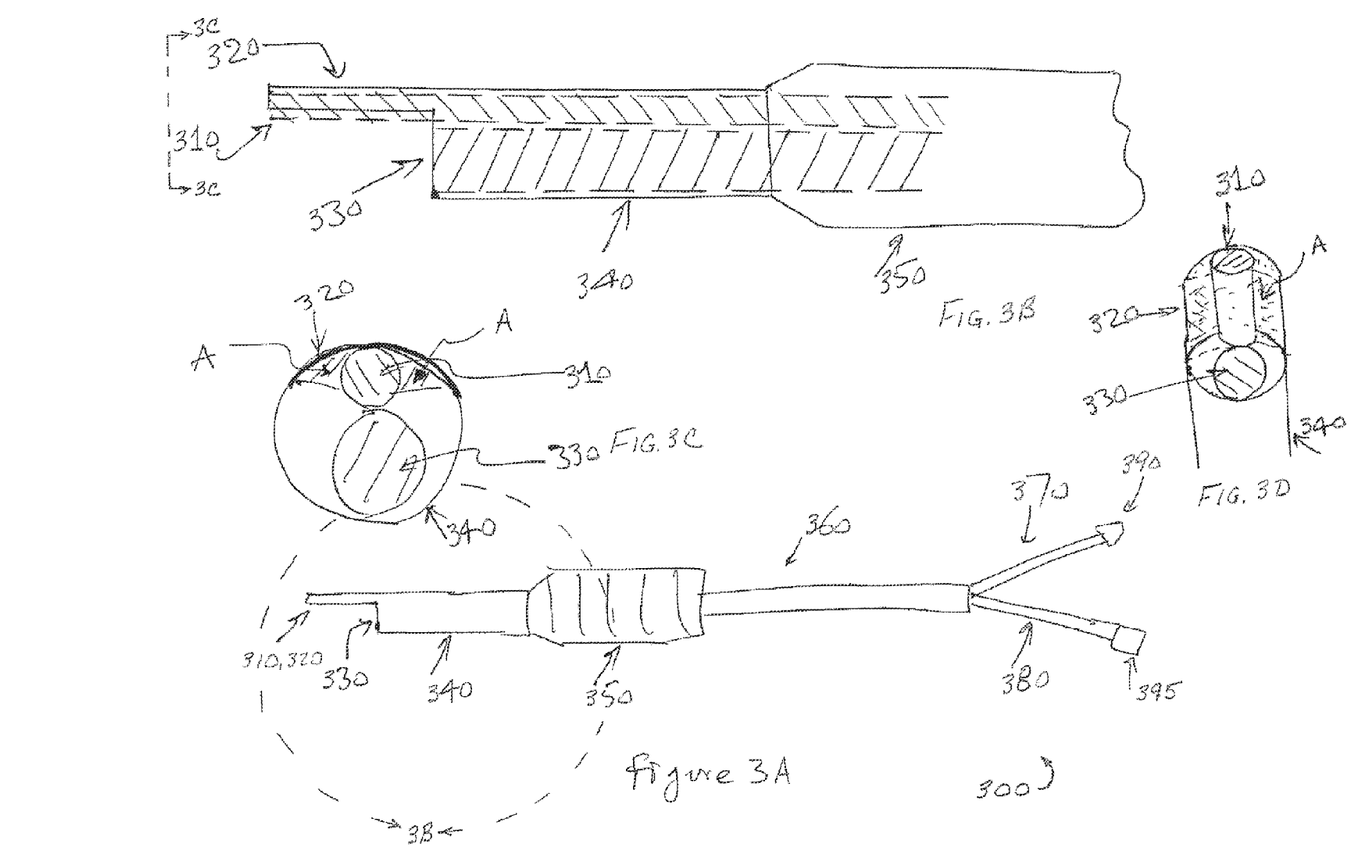
FIG. 3A illustrates a second embodiment of an illumination and laser energy delivery system, including an extended tip laser and illumination probe for retinal surgery, according to the present disclosure.
FIG. 3B illustrates an enlarged view of a portion of the extended tip laser and illumination probe for retinal surgery depicted in FIG. 3A.
FIG. 3C illustrates an enlarged end view of a portion of the extended tip laser and illumination probe for retinal surgery depicted in FIG. 3B.
FIG. 3D illustrates an enlarged, perspective end view of a portion of the extended tip laser and illumination probe for retinal surgery depicted in FIG. 3C.
Figures 4A, 4B, 4C, 4D, 4E:
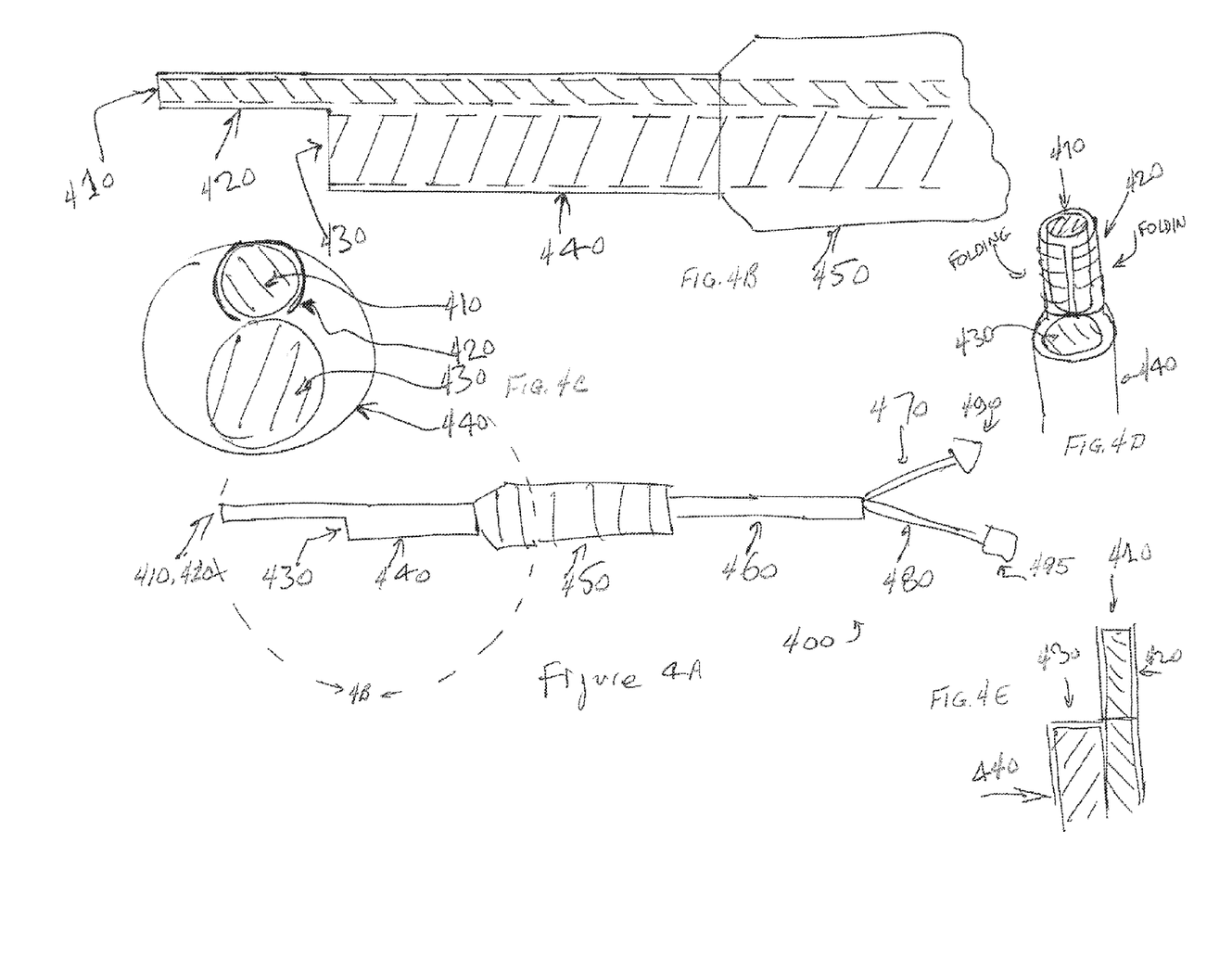
FIG. 4A illustrates an alternative construction of the second embodiment (depicted in FIGS. 3A-3D) of an illumination and laser energy delivery system, including an extended tip laser and illumination probe for retinal surgery, according to the present disclosure.
FIG. 4B illustrates an enlarged view of a portion of the extended tip laser and illumination probe for retinal surgery depicted in FIG. 4A.
FIG. 4C illustrates an enlarged end view of a portion of the extended tip laser and illumination probe for retinal surgery depicted in FIG. 4B.
FIG. 4D illustrates an enlarged, perspective end view of a portion of the extended tip laser and illumination probe for retinal surgery depicted in FIG. 4C.
FIG. 4E illustrates an enlarged, cut away end view of a portion of the extended tip laser and illumination probe for retinal surgery depicted in FIG. 4D.

As illustrated in FIGS. 1A-1B, a representative, prior art illumination and laser energy delivery system 100 is depicted. Laser fiber optic 110 extends beyond probe cannula 140 by approximately 3 mm. Laser fiber optic 110 is protected from breakage by tube 120, typically comprising a stainless steel material. Illumination fiber optic 130 is adjacent laser fiber optic 110 and is contained within probe cannula 140. Illumination fiber optic 130 extends all the way to the illumination source, via hand piece 150, common branch 160, illumination branch 170, and illumination connector 190. Laser fiber optic 110 extends all the way to the laser source, via hand piece 150, common branch 160, laser branch 180, and laser connector 195. As has been noted above, in smaller cannulas (typically, 25 gauge and 23 gauge, as opposed to the larger, 20 gauge cannula) that hold fiber optics for both laser and illumination, less space is available to accommodate the fiber optics. Accordingly, in smaller cannulas, the design tendency has been to reduce the diameter of the illumination and/or laser fibers, which disadvantageously results in lower efficiency levels.

Accordingly, FIGS. 2A-2D depict a first embodiment of an improved illumination and laser energy delivery system 200, including an extended tip laser and illumination probe for retinal surgery. A laser fiber optic 210, preferably polished at both ends, extends beyond probe cannula 240 by approximately 3 mm. Laser fiber optic 210 is protected from breakage by an additional tube or sheath 220 comprising stainless steel, or the like, and/or, in some embodiments, by coating 222. Coating 222 may, in some embodiments, comprise a polyamide. Laser fiber optic 210 extends all the way to connector 295 that connects to the laser machine or laser source.

Illumination tube or ring 230 surrounds laser fiber optic 210 and tube or sheath 220, and is contained within probe cannula 240. Preferably, illumination tube or ring 230 and cannula 240 are flush at the same level, so as not to reduce illumination. In some embodiments, however, illumination tube or ring 230 may extend slightly beyond the end of cannula 240. In such embodiments, illumination tube or ring 230 may require additional protection, for example, via sleeve, sheath, tube, or coating, so as to avoid exceeding the distance where mechanical integrity may be jeopardized and, thereby, to avoid breakage.

The material for illumination tube or ring 230 material is chosen so as to maximize light transmission. Suitable materials comprise glass or high transmission fluoropolymers, such as, but not limited to, fluorinated ethylene propylene ("FEP"), ethylene tetrafluoroethylene ("ETFE"), and polytetrafluoroethylene amorphous fluoropolymers (e.g., TEFLON AF, TEFLON THV, and TEFLON PFA), all of which have light transmissibility ranging, typically, from about 93%-99.9%, in contrast to polymethylmethacrylate ("PMMA") materials that are conventionally used as the fiber optic material for illumination. In order to minimize the losses through illumination tube or ring 230, coatings having different indices of refractions can be applied to the tube or ring inside diameter, outside diameter, or both.

Illumination tube or ring 230 is breached B near the end inside hand piece 250 to allow the face of tube or ring 230 to have full access to the main illumination fiber or fibers. The main illumination fiber extends all the way to the illumination source, via hand piece 250, common branch 260, illumination branch 270, and illumination connector 290. Laser fiber optic 210, 220 extends all the way to the laser source, via hand piece 250, common branch 260, laser branch 280, and laser connector 295.

Advantageously, as illustrated in FIGS. 2A-2D, a very efficient geometry allows the use of most of the area across probe cannula 240.

Further advantageously, embodiments such as those shown and discussed above with regard to FIGS. 2A-2D provide symmetrical lighting around the laser spot at the surgical site, in contrast to prior art devices, wherein laser and illumination fibers disposed next to each other may produce shadows and/or may have lower illumination efficiencies. Such advantages are demonstrated across the range of conventional cannula sizes, including, but not limited to 20 gauge, 23 gauge, and 25 gauge.

It is noted that having a hollow fiber, such as is disclosed herein with regard to illumination tube or ring 230 is a step beyond traditional fiber optic manufacturing. There is a need for such a hollow fiber, which need is normally filled by using multiple fiber optics that are arranged in the shape of a tube. The subject matter of the present disclosure is believed to provide a significant improvement over such multi-fiber tubular arrangements.

Turning now to FIGS. 3A-3D, probe cannula 340 has approximately 3 mm at the tip cut down while preserving part of wall 320. The preserved part of wall 320 is used to provide mechanical protection to one side of laser fiber optic 310. Additional adhesive A may be applied to the gap between laser fiber optic 310 and the preserved part of wall 320, in order to increase the mechanical integrity of the extended portion. It is noted that the depth of the cut may be as much as the mechanical integrity of the remaining extension allows, taking into consideration that an adhesive that bonds the laser fiber optic to the extension may add to the strength and integrity. The depth of the cut contributes to a better spread of the light from the illumination fiber optic and reduces the shadow of the extended tip. The tips of illumination fiber optic 330 and laser fiber optic 310 are contained within probe cannula 340, having the illumination fiber optic 330 and the base of the probe cannula 340, which is approximately 3 mm away from the tip, preferably flush at the same level.

Illumination fiber 330 extends all the way to the illumination source, via hand piece 350, common branch 360, illumination branch 370, and illumination connector 390. Laser fiber optic 310 extends all the way to the laser source, via hand piece 350, common branch 360, laser branch 380, and laser connector 395.

Referring next to FIGS. 4A-4E, this alternative embodiment is similar to that shown in the embodiment of FIGS. 3A-3D, with the following difference: the extended portion of probe cannula 420 is folded around laser fiber optic 410 in order to provide surrounding mechanical protection and stiffening and, in some embodiments, avoiding the need for use of adhesives.

In such embodiments, the depth of the cut is calculated so that, when folded over the laser fiber optic, most of the laser fiber optic is surrounded with the folded extension. Generally, the depth of the cut is approximately equal to $(D/2)*[1+\cos(180*d/D)]$, where d is the diameter of the circle folded over the fiber, D is the diameter of the cannula, and where the depth of the cut is measured along a virtual line passing through the centers of both diameters, with the origin being the intersection of the virtual line with the diameter of the cannula, but on the opposite side of the center of the circle folded over the fiber.

Although a sharp cut at the base of the extension provides a consistent overall diameter of the extension after folding, a rounded cut may, in some embodiments, be preferred. With a rounded cut, the starting point of the cut may start rounded and continues gradually to become a straight cut parallel to the tube length. Such a rounded cut beneficially may provide better strength at the base of the cut and, therefore, increased overall mechanical strength. It is noted that, while such a rounded cut provides increased mechanical integrity, it may reduce the folding length to less than the full length.

It is noted that folding the extended portion requires dedicated and specific tools that are not presently available commercially. Such tools may comprise a wide crimping tool, approximately 3 mm thick, having a round profile and having a hole size appropriate for the final outside diameter of the folded tube. It is also noted that the cutting process on such a small scale is very delicate. Deburring the parts is paramount, as burrs could scratch the side of the fiber optic and, thereby, reduce the output to unacceptable levels.

It is also noted that protecting a fragile fiber or tube, as described herein, without sacrificing significant space is important in applications where cylindrical shapes are required to fit into a confined configuration. Accordingly, the subject matter of the present disclosure is believed to solve one or more important problems not solved by prior art devices.

Having thus described exemplary embodiments of the subject matter of the present disclosure, it is noted that the within disclosures are exemplary only and that various other alternatives, adaptations, and modifications may be made within the scope and spirit of the present invention. Accordingly, the present subject matter is not limited to the specific embodiments as illustrated herein, but is only limited by the following claims.

What is claimed:

1. An extended tip laser and illumination probe for retinal surgery comprising:
    a laser fiber optic;
    an illumination tube or ring surrounding said laser fiber optic about its longitudinal axis;
    said laser fiber optic extending beyond said illumination tube or ring;
    said laser fiber optic and illumination tube or ring disposed within a probe cannula of a surgical hand piece;
    said laser fiber optic connected to a laser source; and
    said illumination tube or ring connected to an illumination source.

2. The probe of claim 1 wherein said illumination tube or ring is disposed proximate the tip of the cannula.

3. The probe of claim 1 wherein said laser fiber optic extends beyond said illumination tube or ring by approximately 3 mm.

4. The probe of claim 1 wherein a back portion of said illumination tube or ring is separated from said laser fiber optic and coupled to one or more fiber optics that provide light to be transmitted to a front of said illumination tube or ring and into the surgical site.

5. The probe of claim 1 wherein said illumination tube or ring can be pre-made or cast.

6. The probe of claim 1 wherein enhancing light output is achieved by coating one or both sides of said illumination tube or ring with a material having an index of refraction differing from an index of refraction of said illumination tube or ring.

7. The probe of claim 1 wherein enhancing light output is achieved by coating one or both sides of said illumination tube or ring with material having one or more index of refraction differing from an index of refraction of said illumination tube or ring.

8. The probe of claim 1 wherein said laser fiber optic extending beyond said illumination tube or ring is at least partially reinforced by a protective material comprising a metal.

9. The probe of claim 8 wherein said protective material comprises stainless steel.

10. The probe of claim 1 wherein said laser fiber optic extending beyond said illumination tube or ring is at least partially reinforced by a protective material comprising a non-metal.

11. The probe of claim 10 wherein said protective material comprises a polymer.

12. The probe of claim 1 wherein said illumination tube or ring is illuminated at the proximal end via a fiber optic which is, in turn, connected to an illumination source, via a hand piece, a common branch, an illumination branch, and an illumination connector.

13. The probe of claim 1 wherein said laser fiber optic is connected to a laser source, via a hand piece, common branch, laser branch, and laser connector.

14. The probe of claim 1 wherein said illumination fiber optic is connected to an illumination source, via a hand piece, a common branch, an illumination branch, and an illumination connector, and wherein said laser fiber optic is connected to a laser source, via a hand piece, common branch, laser branch, and laser connector.

15. The probe of claim 1 wherein the material of said illumination tube or ring is selected from the group consisting of glass or high transmission fluoropolymers, such as, but not limited to, fluorinated ethylene propylene, ethylene tetrafluoro ethylene, and polytetrafluroethylene amorphous fluoropolymers.

16. An extended tip laser and illumination probe for retinal surgery comprising:
    a laser fiber optic, said laser fiber optic contained within a probe cannula of a surgical hand piece;
    said probe cannula cut along its length to form an extension having a proximal and a distal portion;
    a tip of said laser fiber optic approximately flush with said distal portion of said extension; and
    an illumination fiber optic contained within said probe cannula, a tip of said illumination fiber optic approximately flush with said proximal portion of said extension.

17. The probe of claim 16 further comprising means for strengthening said laser fiber optic in association with said extension at least between said proximal and distal portions.

18. The probe of claim 16 wherein said probe cannula is cut approximately 3 mm along its length to form said extension having a proximal and a distal portion.

19. The probe of claim 16 further comprising an adhesive for strengthening said laser fiber optic in association with said extension.

20. The probe of claim 16 wherein said extension is folded about a longitudinal axis of said laser fiber optic for strengthening said laser fiber optic.

21. The probe of claim 16 wherein said illumination fiber optic is connected to an illumination source, via a hand piece, a common branch, an illumination branch, and an illumination connector.

22. The probe of claim 16 wherein said laser fiber optic is connected to a laser source, via a hand piece, common branch, laser branch, and laser connector.

23. The probe of claim 16 wherein said illumination fiber optic is connected to an illumination source, via a hand piece, a common branch, an illumination branch, and an illumination connector, and wherein said laser fiber optic extends to a laser source, via a handpiece, common branch, laser branch, and laser connector.

* * * * *